United States Patent
Zhang et al.

(10) Patent No.: US 11,091,508 B2
(45) Date of Patent: Aug. 17, 2021

(54) FOSAPREPITANT PHOSPHATE INTERMEDIATE AND PREPARATION METHOD THEREFOR

(71) Applicants: Zhejiang Huahai Pharmaceutical Co., Ltd., Zhejiang (CN); Shanghai Aobo Pharmtech, Inc., Ltd., Shanghai (CN)

(72) Inventors: Jicheng Zhang, Shanghai (CN); Zeng Li, Shanghai (CN); Luning Huang, Shanghai (CN); Qian Chen, Shanghai (CN); Anping Tao, Shanghai (CN); Hong Gu, Shanghai (CN)

(73) Assignees: SHANGHAI AOBO PHARMTECH, INC., LTD., Shanghai (CN); ZHEJIANG HUAHAI PHARMACEUTICAL CO., LTD., Zhejiang (CN)

( * ) Notice: Subject to any disclaimer, the term of this patent is extended or adjusted under 35 U.S.C. 154(b) by 57 days.

(21) Appl. No.: 16/099,157

(22) PCT Filed: May 9, 2017

(86) PCT No.: PCT/CN2017/083630
§ 371 (c)(1),
(2) Date: Nov. 5, 2018

(87) PCT Pub. No.: WO2017/193913
PCT Pub. Date: Nov. 16, 2017

(65) Prior Publication Data
US 2019/0144477 A1    May 16, 2019

(30) Foreign Application Priority Data

May 9, 2016 (CN) .......................... 201610300890.7

(51) Int. Cl.
*C07C 213/08* (2006.01)
*C07F 9/6558* (2006.01)
*C07C 215/10* (2006.01)

(52) U.S. Cl.
CPC ........ *C07F 9/65583* (2013.01); *C07C 213/08* (2013.01); *C07C 215/10* (2013.01); *C07F 9/6558* (2013.01)

(58) Field of Classification Search
CPC .................................................... C07F 9/65583
USPC ...................................................... 514/252.18
See application file for complete search history.

(56) References Cited

U.S. PATENT DOCUMENTS 9,072,788 B2 *  7/2015  Blumberg ............ A61K 31/496

FOREIGN PATENT DOCUMENTS

| CN | 104098604 | 10/2014 |
|---|---|---|
| CN | 104650142 | 5/2015 |
| WO | WO2010/018595 | 2/2010 |

OTHER PUBLICATIONS

STN Abstract for U.S. Pat. No. 9,072,788 B2 (2005) Accessed Feb. 26, 2020.*
Translation of CN 104098604 A (Year: 2014).*
Krutikov, V. I. Russian Journal of General Chemistry vol. 82 No. 5, 2012. (Year: 2012).*
International Search Report and Written Opinion for PCT/CN2017/083630 dated Jul. 27, 2017, 10 pages.
English translation of International Search Report for PCT/CN2017/083630 dated Jul. 27, 2017, 2 pages.

* cited by examiner

*Primary Examiner* — Tracy Vivlemore
*Assistant Examiner* — Ebenezer O Sackey
(74) *Attorney, Agent, or Firm* — Sheppard Mullin Richter & Hampton LLP

(57) ABSTRACT

Provided are a fosaprepitant phosphate intermediate (IV) preparation method, a fosaprepitant phosphate intermediate (IV-A) and a method of (AA) for preparing fosaprepitant dimeglumine by using the intermediate (IV-A). IV: $R_1$ and $R_2$ are independently selected from C1-C7 alkyl groups or benzyl groups; IV-A: $R_1$ and $R_2$ are independently selected from C1-C7 alkyl groups, and $R_1$ and $R_2$ are not both benzyl groups.

11 Claims, No Drawings

FOSAPREPITANT PHOSPHATE INTERMEDIATE AND PREPARATION METHOD THEREFOR

CROSS-REFERENCE TO RELATED APPLICATIONS

This application is a U.S. National Stage Application under 35 U.S.C. § 371 of International Application No. PCT/CN2017/083630, filed May 9, 2017, which claims priority to CN 201610300890.7, filed May 9, 2016, the contents of which are incorporated to the present disclosure by reference.

TECHNICAL FIELD

The present invention belongs to the field of medicine, and particularly relates to a fosaprepitant phosphate intermediate and a preparation method thereof, the intermediate is a key intermediate of fosaprepitant dimeglumine (a drug for treating and preventing acute nausea and vomiting caused by chemotherapy), and the present invention also relates to a method for preparing fosaprepitant dimeglumine from such intermediates.

TECHNICAL BACKGROUND

Aprepitant is developed by Merck as the first NK-1 receptor antagonist, which can significantly and effectively prevent acute nausea and vomiting caused by chemotherapy, and its prominent advantages are that it can also be used to prevent vomiting and delayed vomiting during chemotherapy. But aprepitant is insoluble in water and can only be administered orally, sometimes it is difficult to achieve oral administration for patients who would vomit. Fosaprepitant dimeglumine is a prodrug of aprepitant, which is readily soluble in water and rapidly converted into aprepitant in the body, and its clinical efficacy and safety are comparable to those of aprepitant. And fosaprepitant dimeglumine can be formulated as an injection form, which can be administered rectally or intravenously instead of orally, thus fosaprepitant dimeglumine is a good supplement for orally administered aprepitant.

The chemical name of fosaprepitant dimeglumine is 1-deoxy-1-(methylamino)-D-glucitol [3-[[(2R,3S)-2-[(1R)-1-[3,5-bis(trifluoromethyl)phenyl]ethoxy]-3-(4-fluorophenyl)-4-morpholinyl]methyl]-2,5-dihydro-5-oxo-1H-1,2,4-triazol-1-yl]phosphonate, the structural formula thereof is as follows:

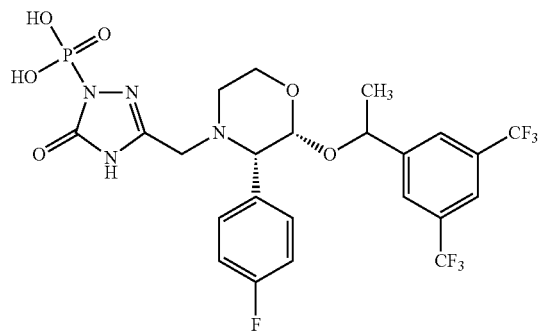

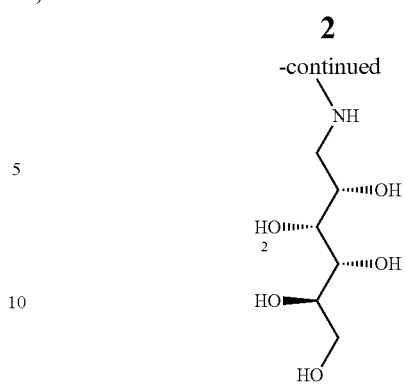

The preparation of fosaprepitant phosphate as an essential intermediate for the preparation of fosaprepitant dimeglumine is a very important part of commercialization. Patents CN1075812C and WO2010018595 all report the same synthesis method, as shown below, reacting aprepitant and tetrabenzyl pyrophosphite under an ultra-low temperature condition, with sodium bis-(trimethylsilyl) amide as a base. The conditions of the whole reaction are relatively strict, the reaction needs to be carried out at a low temperature by using a strong base, the process is complex, strict conditions are required, and the process yield of the method is not high.

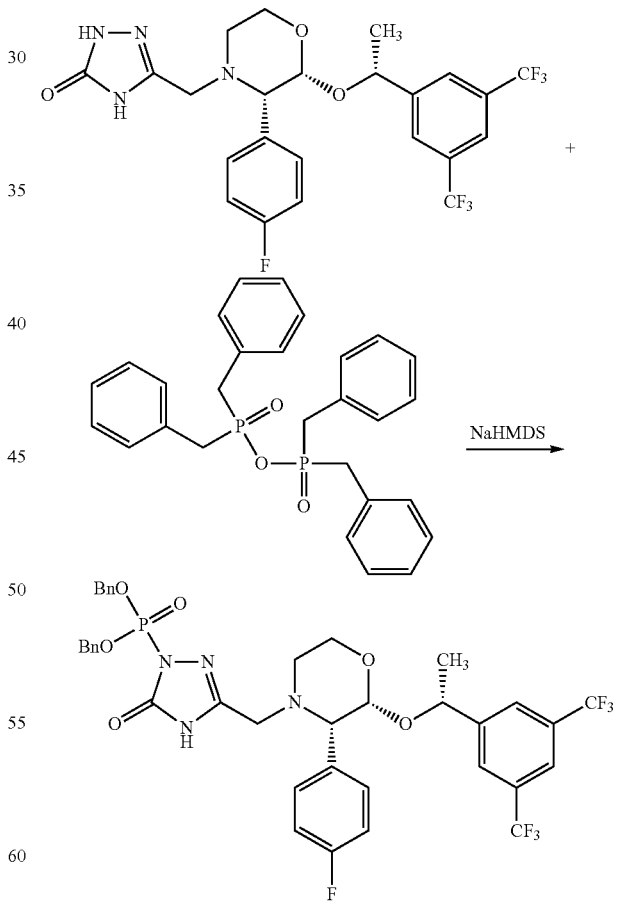

Another synthesis method is reported in patent WO201145817. As shown below, the base and reaction solvent are changed in the method, fosaprepitant phosphate intermediate is prepared by using DMF (N,N-dimethylformamide), sulfolane, DMSO (dimethyl sulfoxide) or NMP (N-methylpyrrolidone) as an solvent and lithium hydroxide, sodium hydroxide, potassium hydroxide, DBU or DBN as a base. Solvents with high boiling points are utilized in the conditions, and a large amount of waste water is produced during post-treatment, the entire process is relatively not environmentally friendly, thus the method is not suitable for mass commercial production.

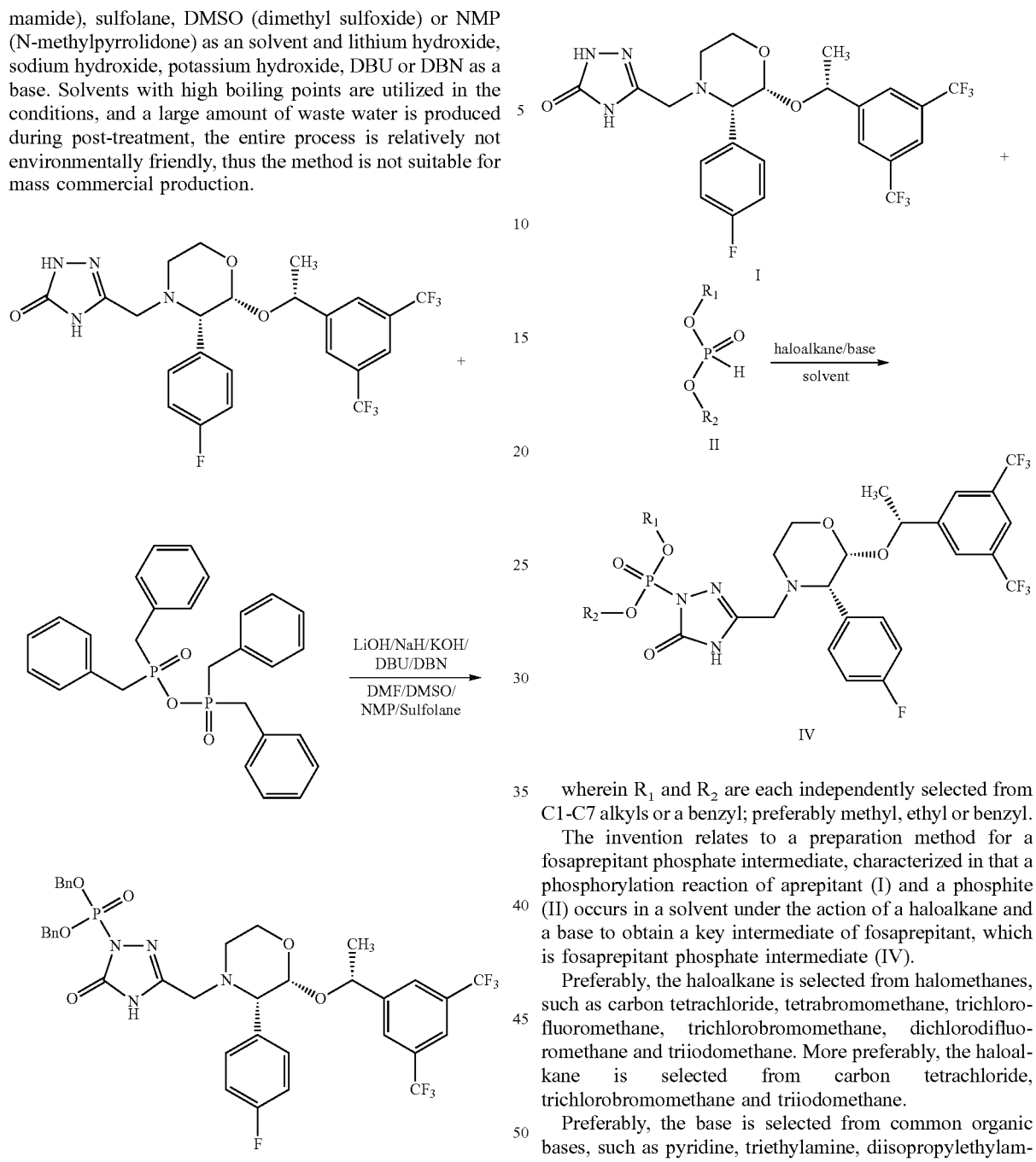

In view of the fact that there are not many preparation routes for fosaprepitant phosphate intermediate and the costs are relatively high currently, it is very necessary to develop a synthesis route with simple process, mild conditions and higher yield.

SUMMARY OF THE INVENTION

The object of the present invention is to provide a preparation method of fosaprepitant phosphate (IV), which has the advantages of easily obtained raw materials, mild conditions, high yield, simple process and being suitable for industrial production. The specific synthesis method is as follows:

wherein $R_1$ and $R_2$ are each independently selected from C1-C7 alkyls or a benzyl; preferably methyl, ethyl or benzyl.

The invention relates to a preparation method for a fosaprepitant phosphate intermediate, characterized in that a phosphorylation reaction of aprepitant (I) and a phosphite (II) occurs in a solvent under the action of a haloalkane and a base to obtain a key intermediate of fosaprepitant, which is fosaprepitant phosphate intermediate (IV).

Preferably, the haloalkane is selected from halomethanes, such as carbon tetrachloride, tetrabromomethane, trichlorofluoromethane, trichlorobromomethane, dichlorodifluoromethane and triiodomethane. More preferably, the haloalkane is selected from carbon tetrachloride, trichlorobromomethane and triiodomethane.

Preferably, the base is selected from common organic bases, such as pyridine, triethylamine, diisopropylethylamine, 4-dimethylaminopyridine and 1,8-diazabicyclo[5.4.0]undec-7-ene (DBU), or common inorganic bases, such as sodium hydroxide, potassium hydroxide, lithium hydroxide, sodium carbonate, potassium carbonate and cesium carbonate; more preferably triethylamine, diisopropylethylamine, 4-dimethylaminopyridine, sodium hydroxide, or potassium hydroxide.

Preferably, the solvent is selected from common polar solvents, such as dichloromethane, acetonitrile, chloroform, tetrahydrofuran and methyl tert-butyl ether.

Preferably, the temperature of the phosphorylation reaction is from −10° C. to 30° C.

Preferably, the molar ratio of aprepitant to phosphite (II) is 1:1 to 1:2; the molar ratio of aprepitant to the haloalkane is 1:2 to 1:10; the molar ratio of aprepitant to the base is 1:1 to 1:2 in the reaction.

The invention further provides a compound of formula IV-A or a pharmaceutically acceptable salt thereof, wherein $R_1$ and $R_2$ are independently selected from methyl, ethyl or benzyl, and $R_1$ and $R_2$ are not both benzyls. Preferably, $R_1$ and $R_2$ are both methyl or are both ethyl, as shown in formula IV-A1 or formula IV-A2. This type of compounds are fosaprepitant phosphate intermediates (IV), which are key intermediates of fosaprepitatant obtained by a phosphorylation reaction of aprepitant (I) and a phosphite (II) in a solvent under the action of a haloalkane (III) and a base.

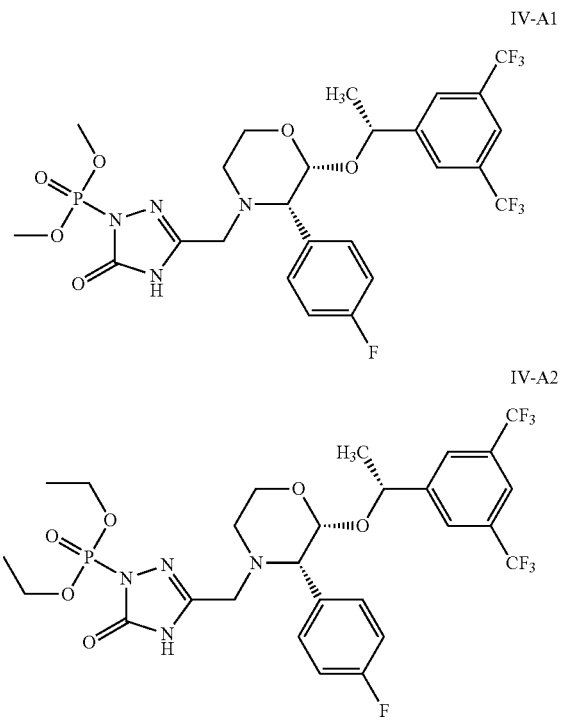

The invention further relates to a method for preparing fosaprepitant dimeglumine by using a compound of formula IV-A, characterized in that:

reacting fosaprepitant phosphate intermediate (IV-A) in a mixture of a solvent and water under the action of a base, and adjusting the pH with an acid solution, filtering then allowing crystallization to obtain fosaprepitant.

Further, reacting the obtained fosaprepitant with N-methyl-D-glucosamine and allowing crystallization to obtain fosaprepitant dimeglumine.

Preferably, the volume ratio of the fosaprepitant phosphate intermediate (IV-A) to the solvent is 1:(5-20); the molar ratio of the fosaprepitant phosphate intermediate (IV-A) to water is 1:(2.0-10.0); the molar ratio of the fosaprepitant phosphate intermediate (IV-A) to the base is 1:(2.0-4.0).

Preferably, the solvent is a lower alcohol, and the lower alcohol in the present invention means an alcohol having 1 to 7 carbon atoms, such as methanol, ethanol or the like, preferably methanol.

Preferably, the base is selected from organic bases or inorganic bases, and the organic bases comprise one or more of pyridine, triethylamine, diisopropylethylamine, 4-dimethylaminopyridine, 1,8-diazabicyclo[5.4.0]undec-7-ene (DBU); the inorganic bases comprise one or more of sodium hydroxide, potassium hydroxide, lithium hydroxide, sodium carbonate, potassium carbonate, cesium carbonate; preferably sodium hydroxide or potassium hydroxide.

Preferably, the acid solution is a 1N to 3N solution of hydrochloric acid in the solvent.

Preferably, the pH is adjusted to 1 to 2.

Compared with the prior art, the preparation method of a fosaprepitant phosphate intermediate (IV) of the present invention has the advantages of easily obtained raw materials, mild conditions, high yield, simple process, etc., the method reduces the production cost and is beneficial to industrial production.

EMBODIMENTS

In order to further understand the present invention, the embodiments of the present invention will be described with combination of the following examples. However, it should be noted that these descriptions are only intended to further illustrate the features and advantages of the present invention, and are not intended to limit the claims of the present invention. The starting material used in the present invention, aprepitant, can be purchased in bulk.

Example 1: Fosaprepitant Phosphate Intermediate (IV, Wherein $R_1$ and $R_2$ are Benzyls)

Into a 500 mL reaction flask, 200 mL of dichloromethane and 20 g of aprepitant (I) were added, and the mixture was stirred until dissolved at 25° C. Then 9.8 g of dibenzyl phosphite and 11.5 g of carbon tetrachloride were added successively, the reaction was cooled to 0-5° C., 3.79 g of triethylamine was added dropwise, and the reaction was kept at 0-10° C. for 16-24 hours until TLC showed that the starting materials disappeared. Dilute hydrochloric acid was added to the reaction solution to adjust the pH to neutral, 100 mL of water was added thereto, followed by two times of extraction with 200 mL of dichloromethane for each time. The dichloromethane layers were combined and washed with 100 mL of 5% NaCl solution for two times, dried over anhydrous magnesium sulfate and then pulped with methyl tert-butyl ether to obtain 27.5 g of fosaprepitant phosphate intermediate (IV) in a yield of 92.4%. $^1$H NMR (400 MHz, CDCl3): δ 1.15-1.25 (m, 2H), 1.45 (d, 3H), 2.48 (td, 1H), 2.75 (d, 1H), 2.86 (d, 2H), 3.2 (m, 1H), 3.46 (m, 2H), 3.64 (m, 1H), 4.19 (td, 1H), 4.30 (d, 1H), 4.87 (q, 1H), 5.22 (m, 4H), 7.07 (d, 2H), 7.12 (s, 2H), 7.28 (m, 4H), 7.34 (m, 4H), 7.63 (s, 1H), 9.44 (s, 1H). Mass: 795.2 [M+H]$^+$.

Example 2: Fosaprepitant Phosphate Intermediate (IV, wherein $R_1$ and $R_2$ are methyls)

Into a 500 mL reaction flask, 100 mL of methyl tert-butyl ether and 10 g of aprepitant (I) were added, and the mixture was stirred until dissolved at 25° C. Then 3.1 g of dimethyl phosphite and 18.6 g of trichlorobromomethane were added successively, the reaction was cooled to 0-5° C., 3.6 g of diisopropylethylamine was added dropwise, the temperature of the reaction was raised to 20-30° C. and the reaction was kept at the temperature for 16-24 hours until TLC showed that the starting materials disappeared. Dilute hydrochloric acid was added to the reaction solution to adjust the pH to neutral, 50 mL of water was added thereto, followed by two times of extraction with 100 mL of dichloromethane for each time. The dichloromethane layers were combined and washed with 50 mL of 5% NaCl solution for two times, dried over anhydrous magnesium sulfate and then pulped with methyl tert-butyl ether to obtain 10.9 g of fosaprepitant phosphate intermediate (IV, wherein $R_1$ and $R_2$ are methyls) in a yield of 90.6%. $^1$H NMR (400 MHz, CDCl3) δ 8.08 (s, 1H), 7.77 (q, J=1.8 Hz, 1H), 7.64 (t, J=2.1 Hz, 1H), 7.37 (dt, J=3.0, 1.5 Hz, 1H), 7.31 (ddd, J=7.1, 5.8, 1.1 Hz, 2H), 7.18-7.10 (m, 2H), 5.58 (d, J=7.0 Hz, 1H), 4.68 (qt, J=6.8, 1.0 Hz, 1H), 4.17-4.00 (m, 3H), 3.98 (dt, J=7.0, 1.0 Hz, 1H), 3.81 (d, J=12.5 Hz, 1H), 3.39 (d, J=10.8 Hz, 6H), 2.93 (ddd, J=12.5, 11.2, 3.5 Hz, 1H), 2.44 (dt, J=12.6, 1.8 Hz, 1H), 1.49 (d, J=6.9 Hz, 3H). Mass: 643.1 [M+H]$^+$.

Example 3: Fosaprepitant Phosphate Intermediate (IV, Wherein $R_1$ and $R_2$ are Ethyls)

Into a 500 mL reaction flask, 133 mL of chloroform and 13.3 g of aprepitant (I) were added, and the mixture was stirred until dissolved at 25° C. Then 6.87 g of diethyl phosphite and 98.0 g of triiodomethane were added successively, and the reaction was cooled to 0-5° C., 6.1 g of 4-dimethylaminopyridine was added dropwise, the temperature of the reaction was raised to 10-20° C. and the reaction was kept at the temperature for 16-24 hours until TLC showed that starting materials disappeared. Dilute hydrochloric acid was added to the reaction solution to adjust the pH to neutral, 130 mL of water was added thereto, followed by two times of extraction with 270 mL of dichloromethane for each time. The dichloromethane layers were combined and washed with 130 mL of 5% NaCl solution for two times, dried over anhydrous magnesium sulfate and then pulped with methyl tert-butyl ether to obtain 15.1 g of fosaprepitant phosphate intermediate (IV, wherein $R_1$ and $R_2$ are ethyls) in a yield of 90.4%. $^1$H NMR (400 MHz, CDCl3) δ 8.13 (s, 1H), 7.77 (q, J=1.7 Hz, 1H), 7.64 (q, J=2.5, 2.0 Hz, 1H), 7.37 (t, J=1.8 Hz, 1H), 7.31 (ddd, J=7.0, 5.8, 1.1 Hz, 2H), 7.14 (dd, J=8.9, 7.5 Hz, 2H), 5.59 (d, J=6.9 Hz, 1H), 4.73-4.64 (m, 1H), 4.18-4.02 (m, 5H), 4.04-3.95 (m, 2H), 3.92-3.78 (m, 2H), 3.64 (dp, J=12.5, 8.1 Hz, 1H), 2.94 (ddd, J=12.5, 11.1, 3.5 Hz, 1H), 2.43 (dt, J=12.7, 1.9 Hz, 1H), 1.49 (d, J=6.9 Hz, 3H), 1.20 (t, J=8.0 Hz, 3H), 1.12 (t, J=7.9 Hz, 3H). Mass: 671.2 [M+H]$^+$.

Example 4: Fosaprepitant Phosphate Intermediate (IV, Wherein $R_1$ and $R_2$ are Benzyls)

Into a 500 mL reaction flask, 200 mL of acetonitrile and 20 g of aprepitant (I) were added, and the mixture was stirred until dissolved at 25° C. Then 14.7 g of dibenzyl phosphite and 28.9 g of carbon tetrachloride were added successively, and the reaction was cooled to −10-0° C., 25 mL aqueous solution of 3.1 g KOH was added dropwise, and the reaction was kept at 0-10° C. for 16-24 hours until TLC showed that starting materials disappeared. Dilute hydrochloric acid was added to the reaction solution to adjust the pH to neutral, 100 mL of water was added thereto, followed by two times of extraction with 200 mL of dichloromethane for each time. The dichloromethane layers were combined and washed with 100 mL of 5% NaCl solution for two times, dried over anhydrous magnesium sulfate and then pulped with methyl tert-butyl ether to obtain 25.8 g of fosaprepitant phosphate intermediate (IV) in a yield of 88.4%. $^1$H NMR (400 MHz, CDCl3): δ 1.15-1.25 (m, 2H), 1.45 (d, 3H), 2.48 (td, 1H), 2.75 (d, 1H), 2.86 (d, 2H), 3.2 (m, 1H), 3.46 (m, 2H), 3.64 (m, 1H), 4.19 (td, 1H), 4.30 (d, 1H), 4.87 (q, 1H), 5.22 (m, 4H), 7.07 (d, 2H), 7.12 (s, 2H), 7.28 (m, 4H), 7.34 (m, 4H), 7.63 (s, 1H), 9.44 (s, 1H). Mass: 795.2 [M+H]$^+$.

Example 5: Fosaprepitant Phosphate Intermediate (IV, Wherein $R_1$ and $R_2$ are Benzyls)

Into a 500 mL reaction flask, 200 mL of tetrahydrofuran and 20 g of aprepitant (I) were added, and the mixture was stirred until dissolved at 25° C. Then 12.8 g of dibenzyl phosphite and 28.9 g of carbon tetrachloride were added successively, the reaction was cooled to −10-0° C., 20 mL aqueous solution of 2.5 g NaOH was added dropwise, and the reaction was kept at 0-10° C. for 16-24 hours until TLC showed that starting materials disappeared. Dilute hydrochloric acid was added to the reaction solution to adjust the pH to neutral, 100 mL of water was added thereto, followed by two times of extraction with 200 mL of dichloromethane for each time. The dichloromethane layers were combined and washed with 100 mL of 5% NaCl solution for two times, dried over anhydrous magnesium sulfate and then pulped with methyl tert-butyl ether to obtain 26.2 g of fosaprepitant phosphate intermediate (IV) in a yield of 89.8%. $^1$H NMR (400 MHz, CDCl3): δ 1.15-1.25 (m, 2H), 1.45 (d, 3H), 2.48 (td, 1H), 2.75 (d, 1H), 2.86 (d, 2H), 3.2 (m, 1H), 3.46 (m, 2H), 3.64 (m, 1H), 4.19 (td, 1H), 4.30 (d, 1H), 4.87 (q, 1H), 5.22 (m, 4H), 7.07 (d, 2H), 7.12 (s, 2H), 7.28 (m, 4H), 7.34 (m, 4H), 7.63 (s, 1H), 9.44 (s, 1H). Mass: 795.2 [M+H]$^+$.

Example 6: Fosaprepitant Phosphate Intermediate (IV, Wherein $R_1$ is Benzyl and $R_2$ is Methyl)

Into a 500 mL reaction flask, 200 mL of dichloromethane and 20 g of aprepitant (I) were added, and the mixture was stirred until dissolved at 25° C. Then 9.8 g of benzyl-methyl phosphite and 15.0 g of carbon tetrachloride were added successively, the reaction was cooled to 0-5° C., 3.8 g of triethylamine was added dropwise, and the reaction was kept at 0-10° C. for 16-24 hours until TLC showed that starting materials disappeared. Dilute hydrochloric acid was added to the reaction solution to adjust the pH to neutral, 100 mL of water was added thereto, followed by two times of extraction with 200 mL of dichloromethane for each time. The dichloromethane layers were combined and washed with 100 mL of 5% NaCl solution for two times, dried over anhydrous magnesium sulfate and then pulped with methyl tert-butyl ether to obtain 21.7 g of fosaprepitant phosphate intermediate (IV, wherein $R_1$ is benzyl and $R_2$ is methyl) in a yield of 81.1%. $^1$H NMR (500 MHz, Chloroform-d) δ 8.01 (s, 1H), 7.77 (t, J=1.8 Hz, 1H), 7.65-7.61 (m, 1H), 7.50 (dq, J=1.9, 1.0 Hz, 1H), 7.47-7.41 (m, 2H), 7.41-7.29 (m, 5H), 7.26-7.18 (m, 2H), 5.51 (d, J=6.9 Hz, 1H), 5.03 (dd, J=8.5, 1.7 Hz, 2H), 4.73 (dd, J=6.9, 1.0 Hz, 1H), 3.95 (dd, J=15.9, 12.0 Hz, 2H), 3.73 (dt, J=6.9, 1.1 Hz, 1H), 3.66 (d, J=12.2 Hz, 1H), 3.39 (d, J=10.8 Hz, 3H), 1.52 (d, J=6.8 Hz, 3H). Mass: 719.2 [M+H]$^+$.

Example 7: Preparation of Fosaprepitant Dimeglumine from a Fosaprepitant Phosphate Intermediate (IV, Wherein $R_1$ and $R_2$ are Methyls)

15.3 g of the fosaprepitant phosphate intermediate (IV, wherein $R_1$, $R_2$ are methyls) prepared according to Example 2 was dissolved in 120 mL of methanol, 5.8 g of KOH and 1.2 g of water were added, the temperature was raised to 25-30° C., and the reaction was kept at the temperature for 20 hours until the starting materials were completely converted. Cooled to room temperature, then the pH was slowly adjusted to pH=1 with a 2N hydrochloric acid methanol solution, and the precipitated solid was removed by filtration. After concentrating the methanol and replacing the same with 38 mL of methyl tert-butyl ether, allowing crystallization and solid fosaprepitant was obtained after filtration. The above solid was dissolved in 44 mL of methanol, 10.2 g of N-methyl-D-glucosamine was added, after stirring at room temperature for 2-3 hours, the solution was slowly added dropwise into 132 mL of isopropanol, and crystallization was allowed to obtain 19.1 g of fosaprepitant dimeglumine in a yield of 83.4%. Mass: 615.4 [M+H]$^+$.

Example 8: Preparation of Fosaprepitant Dimeglumine from a Fosaprepitant Phosphate Intermediate (IV, Wherein $R_1$ and $R_2$ are Ethyls)

10.5 g of the fosaprepitant phosphate intermediate (IV, wherein $R_1$ and $R_2$ are ethyls) prepared according to Example 3 was dissolved in 120 mL of methanol, 2.5 g of NaOH and 1.1 g of water were added, the temperature was raised to 25-30° C., and the reaction was kept at the temperature for 36 hours until the starting materials were completely converted. Cooled to room temperature, then the pH was slowly adjusted to pH=1 with a 2N hydrochloric acid methanol solution, and the precipitated solid was removed by filtration. After concentrating the methanol and replacing the same with 30 mL of methyl tert-butyl ether, allowing crystallization, and solid fosaprepitant was obtained after filtration. The above solid was dissolved in 29 mL of methanol, 6.7 g of N-methyl-D-glucosamine was added, after stirring at room temperature for 2-3 hours, the solution was slowly added dropwise into 87 mL of isopropanol, and crystallization was allowed to obtain 12.9 g of fosaprepitant dimeglumine in a yield of 82.2%. Mass: 615.4 [M+H]$^+$.

The preparation method of a fosaprepitant phosphate intermediate proposed by the present invention has been described by examples, and it will be apparent to a person skilled in the art to modify, appropriately alter and combine the preparation methods of fosaprepitant phosphate intermediates described herein to implement the technology of the present invention without departing from the content, spirit and scope of the present invention. It should be noted particularly that all similar alternatives and modifications are obvious to a person skilled in the art and are considered to be included in the spirit, scope and content of the present invention.

The invention claimed is:

1. A preparation method for a fosaprepitant phosphate intermediate (IV), wherein a phosphorylation reaction of aprepitant (I) and a phosphite (II) occurs in a solvent under the action of a haloalkane and a base to obtain the fosaprepitant phosphate intermediate (IV), wherein $R_1$ and $R_2$ are independently selected from C1-C7 alkyls or benzyl:

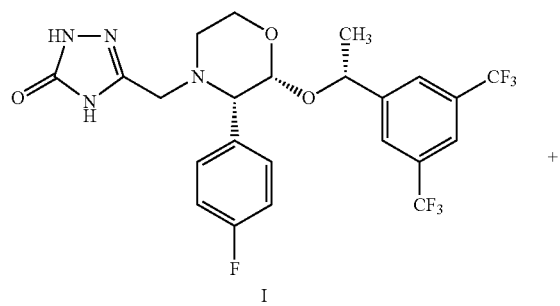

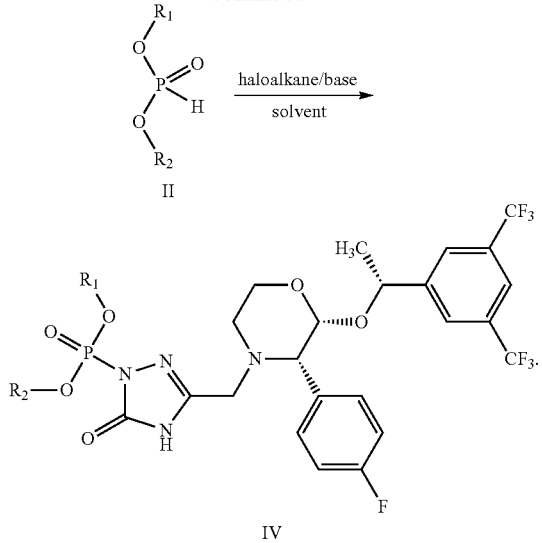

2. The preparation method according to claim 1, wherein the $R_1$ and $R_2$ are independently selected from methyl, ethyl or benzyl.

3. The preparation method according to claim 1, wherein the haloalkane is selected from the group consisting of carbon tetrachloride, tetrabromomethane, trichlorofluoromethane, trichlorobromomethane, dichlorodifluoromethane and triiodomethane.

4. The preparation method according to claim 1, wherein the base is a common organic base or a common inorganic base.

5. The preparation method according to claim 1, wherein the solvent is selected from dichloromethane, acetonitrile, chloroform, tetrahydrofuran and methyl tert-butyl ether.

6. The preparation method according to claim 1, wherein the temperature of the phosphorylation reaction is −10° C. to 30° C.

7. The preparation method according to claim 1, wherein the molar ratio of aprepitant to the phosphite is 1:1 to 1:2.

8. The preparation method according to claim 1, wherein the molar ratio of aprepitant to the haloalkane is from 1:2 to 1:10.

9. The preparation method according to claim 1, wherein the molar ratio of aprepitant to the base is from 1:1 to 1:2.

10. The preparation method according to claim 4, wherein the base is selected from the group consisting of pyridine, triethylamine, diisopropylethylamine, 4-dimethylaminopyridine and 1,8-diazabicyclo[5.4.0]undec-7-ene (DBU), or the base is selected from the group consisting of sodium hydroxide, potassium hydroxide, lithium hydroxide, sodium carbonate, potassium carbonate and strontium carbonate.

11. The preparation method according to claim 4, wherein the base is selected from the group consisting of pyridine, triethylamine, diisopropylethylamine, 4-dimethylaminopyridine and 1,8-diazabicyclo[5.4.0]undec-7-ene (DBU).

* * * * *